United States Patent [19]

North, Jr.

[11] 3,931,018

[45] Jan. 6, 1976

[54] ASSEMBLY FOR COLLECTION, SEPARATION AND FILTRATION OF BLOOD

[75] Inventor: Howard North, Jr., Newfoundland, N.J.

[73] Assignee: Becton, Dickinson and Company, East Rutherford, N.J.

[22] Filed: Aug. 9, 1974

[21] Appl. No.: 496,029

[52] U.S. Cl. ............... 210/359; 210/516; 210/518; 210/DIG. 23
[51] Int. Cl.² ........................................ B01D 33/00
[58] Field of Search ....... 23/230 B, 258.5, 259, 292; 128/214 R, 218 M, 272; 210/83, 84, 109, 131, 359, 514–518, DIG. 23, DIG. 24; 233/1 A, 1 R, 26

[56] References Cited
UNITED STATES PATENTS

| | | | |
|---|---|---|---|
| 2,305,278 | 12/1942 | Smith | 128/218 M |
| 3,508,653 | 4/1970 | Coleman | 210/DIG. 23 |
| 3,537,605 | 11/1970 | Solowey | 128/218 M |
| 3,661,265 | 5/1972 | Greenspan | 210/359 |
| 3,667,652 | 6/1972 | Morane et al. | 128/218 M |
| 3,699,961 | 10/1972 | Szpur | 128/218 M |
| 3,779,383 | 12/1973 | Ayres | 210/516 X |
| 3,814,258 | 6/1974 | Ayres | 210/DIG. 23 |

*Primary Examiner*—Charles N. Hart
*Assistant Examiner*—Robert H. Spitzer
*Attorney, Agent, or Firm*—Kane, Dalsimer, Kane, Sullivan and Kurucz

[57] ABSTRACT

Devices are disclosed which are useful in the simultaneous separation and filtration of the liquid portion of clotted whole blood and anti-coagulant treated whole blood. The devices are employed in novel apparatus of the invention, for the collection, separation and filtration of blood serum and blood plasma from clotted whole blood and anti-coagulant treated whole blood, respectively.

14 Claims, 7 Drawing Figures

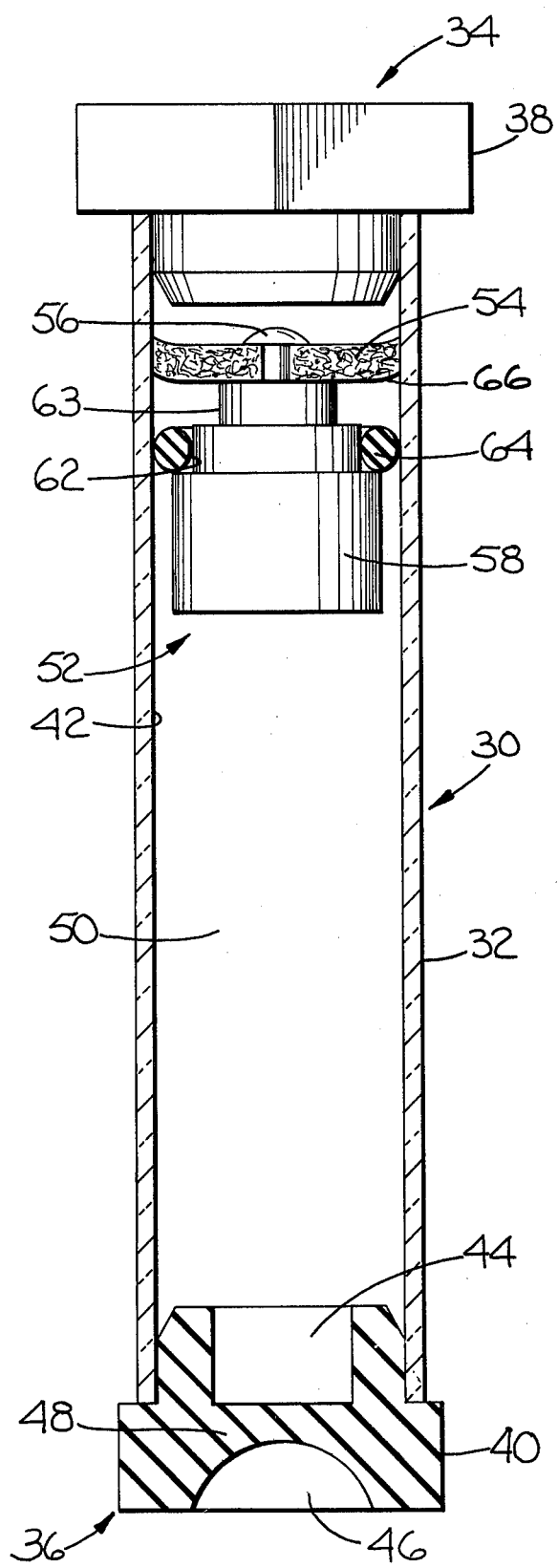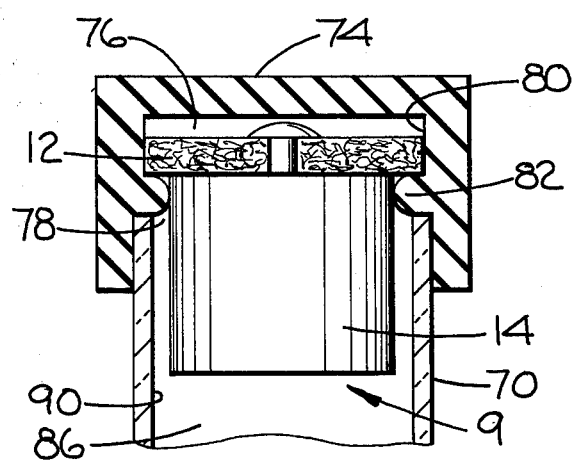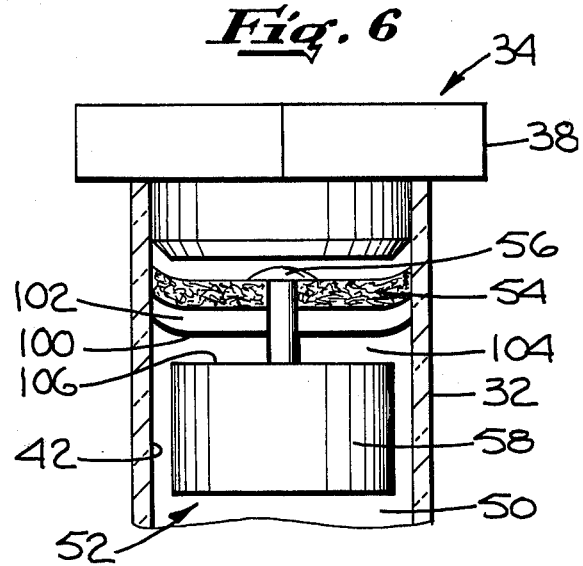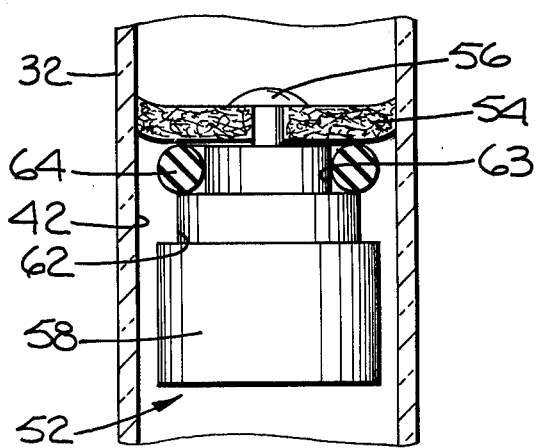

3,931,018

ASSEMBLY FOR COLLECTION, SEPARATION AND FILTRATION OF BLOOD

BACKGROUND OF THE INVENTION

1. Field of the Invention

The invention concerns devices and apparatus for the separation of blood serum and blood plasma, with the aid of centrifugal force, from whole blood mixtures.

2. Brief Description of the Prior Art

Devices and apparatus for the separation of blood serum and blood plasma from clotted whole blood and anticoagulant treated whole blood, respectively, by the aid of centrifugal force have been known prior to my invention. Representative of such devices are those disclosed in U.S. Pat. No. 3,508,653.

In general, the devices of the prior art employ a solid, elastomeric plug or piston which may or may not have a filter element mounted therein. The elastomeric piston forms a sliding seal with the inner walls of a tubular container for the blood mixture to be separated. The disadvantage of prior art devices employing solid elastomeric plugs as pistons resides in the fact that they must meet dimensional specifications of a very narrow range in order that a proper and effective seal is obtained between the collection container wall and the piston member.

The devices and assemblies of my invention are relatively simple in construction, and do not require the precise dimensional specifications of solid piston members previously employed for the separation of blood plasma or blood serum.

SUMMARY OF THE INVENTION

The invention comprises a device for the simultaneous filtration and separation of the liquid phase of blood from the substantially cellular phase thereof which comprises; a cylindrical filter member having a solid mass attached to the central portion of one end, said member and said mass together having a specific gravity within the range of from 1.03 to about 1.09.

The invention also comprises unitary, self-contained assemblies for the separation of blood serum and plasma from whole blood, which employ the devices of the invention as components thereof.

BRIEF DESCRIPTION OF THE DRAWINGS

FIG. 4 is a cross-sectional side elevation of an assembly of the invention.

FIG. 5 is a fragmentary cross-sectional side elevation of an alternate embodiment assembly of the invention.

FIG. 6 is a fragmentary cross-sectional view of an alternate embodiment.

FIG. 7 is a fragmentary view of the assembly in FIG. 4 but after initial centrifugation.

DETAILED DESCRIPTION OF THE INVENTION

A complete understanding of the invention is conveniently obtained by referring to those embodiments illustrated in the accompanying drawings.

Figure 1:
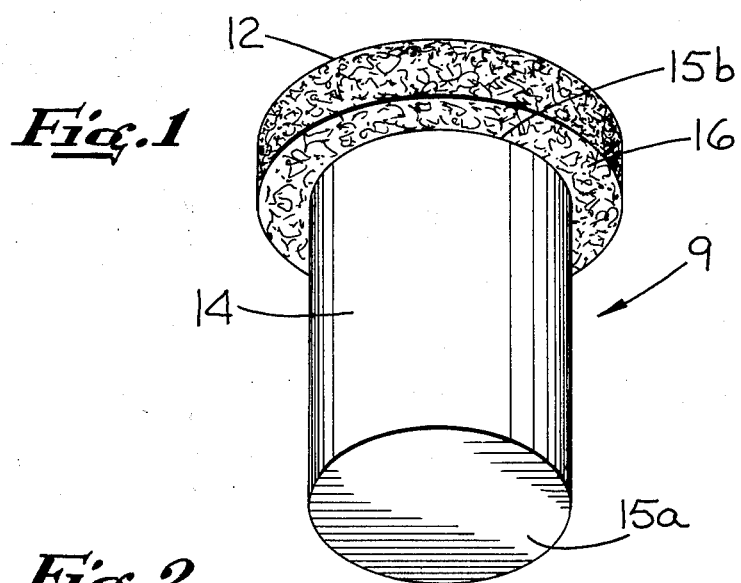
FIG. 1 is a view in perspective of an embodiment device of the invention.

FIG. 1 is a view in perspective of a representative device of the invention. The device is a piston 9 which comprises a cylindrical filter member 12 having attached to one end a cylindrical mass 14. The mass 14 is of a lesser diameter than filter member 12 and is attached to the center of filter member 12 so that the periphery 16 of filter member 12 radiates beyond the body of mass 14. Filter member 12 may be any flexible filtration material which is inert to blood or reagents employed in the collection, storage and analysis of blood material. For example, filter member 12 may be fabricated from flexible porous plastic such as porous polyethylene, porous polyurethane, porous tetrafluoroethylene and the like; fiberglas in the form of woven sheets or batts; woven asbestos and like filtration materials. The filter materials employed will generally have pores which permit the passage of the liquid phase of a blood mixture but prevent passage of the insoluble, substantially cellular blood phase. In general, the pores of the filter deny passage of solid and semi-solid particulate material having a spherical diameter of greater than about 50 microns. Preferred as a flexible filter material is a disc fabricated of open cell polyurethane foam having the above described porosity. This preference is based not only upon its suitability as a filter element, but also on its resiliency in shape as will be described more fully hereinafter. Most preferred as a filter material is a relatively dense polyurethane foam having pore sizes on the order of about 50 microns or less, i.e.; having a density of from about 15 to about 40 lbs. per cubic foot.

Mass 14 may be fabricated of any body or material which is inert to reaction with blood, blood constituents and reagents commonly employed in treating or analyzing blood. Illustrative of materials which may be used to fabricate mass 14 are polymeric materials such as acrylonitrile-butadienestyrene (ABS), polyacrylates, polycarbonates, polystyrene and the like. The density and dimensions of mass 14 are selected so as to provide the combination of mass 14 and filter 12 with an overall specific gravity of from about 1.03 to about 1.09, preferably from about 1.03 to about 1.05. The preferred shape of mass 14 is such that the length of mass 14 between ends 15a and 15b exceeds the diameter of the filter member 12. This assures that the device of the invention will be stable in operation as will be described hereinafter. Mass 14 may be hollow or solid in cross-section. Preferably mass 14 is a solid cylinder.

As shown in FIG. 1, mass 14 is attached to the lower end of filter 12 at the center thereof so as to leave exposed peripheral margin 16. Mass 14 may be attached to filter member 12 in any conventional manner, i.e.; by adhesive, staples, pins and like conventional means of attachment.

Figure 2:
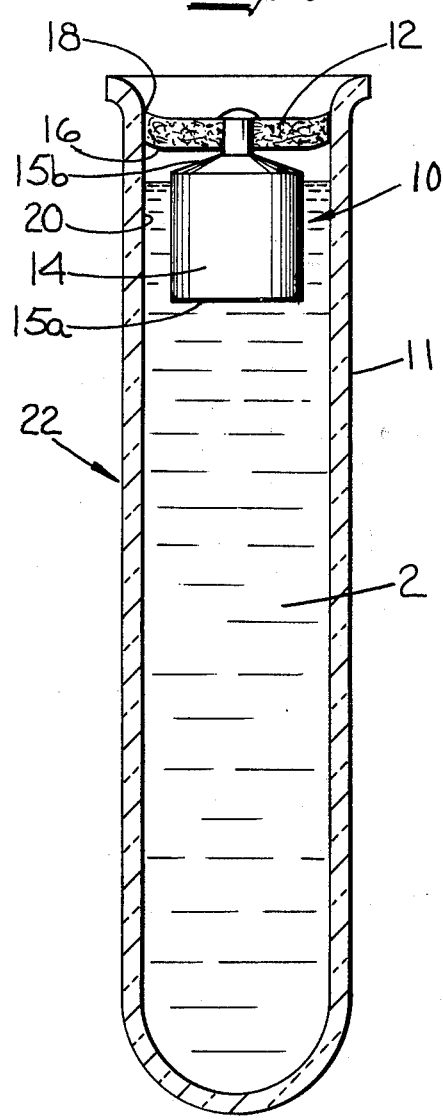
FIG. 2 is a cross-sectional side elevation of a preferred embodiment of the device of FIG. 1, shown in use, prior to the separation and filtration of the liquid phase of a blood specimen.
Figure 3:
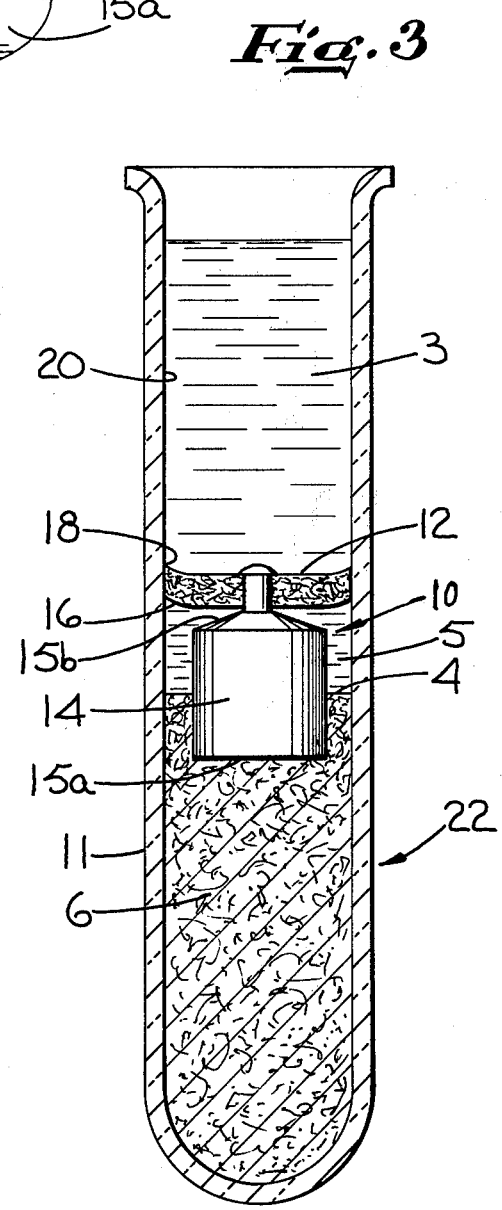
FIG. 3 is a view as in FIG. 2 but following separation and filtration of the blood specimen.

The method of using the device of the invention is illustrated in FIGS. 2 and 3. FIG. 2 is a cross-sectional view of a blood collection tube 11 containing blood 2 which is to be separated by centrifugation into blood plasma or serum 5 and substantially cellular portion 6. The piston-like device 10 has been inserted into the open end of the tube 11. Device 10 is a preferred embodiment device of the invention differing from the device 9 shown in FIG. 1 only in that the end 15b adjacent to the filter member 12 is substantially cone shaped, to facilitate the complete descent of solid particulate matter which might otherwise adhere to mass 14. The dimensions of device 10 are such that filter member 12 periphery 16 lightly impinges upon the inner wall 20 of tube 11 to form a sliding fit 18 by a slight compression of the resilient and flexible filter member 12 at periphery 16. The flexibility of member 12 allows it to flex upward on insertion so that there is only a light pressure of member 12 upon the inner wall 20 of tube 11. With device 10 in place, the entire assembly 22 is centrifuged in a conventional manner to effect separation of the blood into its component liquid and substantially cellular phases. During centrifugation, device 10 is carried down tube 11 into the interface 4 between the separated liquid 5 and solids 6 as seen in FIG. 3. During descent, the serum or plasma 5 displaced by descending device 10 is forced through the pores of filter member 12 in the area of periphery 16. As the serum or plasma 5 passes through filter 12 it is filtered so that serum or plasma 3 above device 10 is filtered so as to be substantially free of any particulate matter which may have remained suspended in the serum or plasma following centrifugation.

The specific gravity of device 10 is between about 1.03 and 1.09, preferably between 1.03 and 1.05. This specific gravity is generally less than the substantially solid portion 6 but more than the liquid portion 5 of the blood mixture separated. Thus, during centrifugation, device 10 automatically comes to rest in the area of the interface 4 between the relatively heavy solid phase 6 and the substantially lighter liquid portion 5.

Generally, device 10 has sufficient interference fit between the inner wall 20 of collection tube 11 and the periphery 16 of filter member 12 so that the filtered serum 3 can be decanted from tube 11 following separation and filtration of the serum or plasma 3 without moving the piston 10. Filter member 12 in its deflected position forms the well-known mechanical toggle which greatly increases the friction force to be overcome for withdrawal, thereby holding device 10 in position at interface 4 during decantation of the filtered serum 3.

During descent of device 10 within tubular container 11, filter member 12 is maintained substantially in the same position as shown in FIGS. 2 and 3, i.e.; having its upper and lower surfaces substantially parallel to the plane normal to the long axis of tube 11. Stabilization and maintenance of filter member 12 in this position whereby periphery 16 maintains a sliding engagement with the inner wall 20 of tube 11 is one of the functions of mass 14 and is obtained by placement of mass 14 to put the center of gravity of device 10 precisely along the longitudinal axis of the center of tube 11. When the preferred mass 14 is employed, i.e.; one having a length exceeding the diameter of member 12 and having a close (but not impinging) diametral fit with the inner wall 20 of tube 11, tumbling of device 10 is obviated, thereby serving to keep periphery 16 of filter member 12 in contact with the walls 20 of tube 11.

FIG. 4 is a cross-sectional side elevation of a unitary, self-contained assembly which comprises a preferred embodiment of the invention for the collection, separation, filtration and storage of blood. The assembly, generally referred to by the numeral 30 comprises a tubular container 32 having open ends 34 and 36 which are fitted with closures 38 and 40, respectively. Closure 38 is an elastomeric stopper which forms a compression fit with the inner walls 42 of tube 32. Closure 40 is similarly held in end 36 by a compression fit. Closures 38 and 40 have an annular recess 44 in their inner surface and a recess 46 in their outer surface, to provide a thin penetrable zone 48. Thin penetrable zone 48 provides a zone for inserting a cannula into chamber 50 defined by tube 32.

Mounted in tube 32 at the end distal to closure 40 is an alternate device 52 embodiment of the invention which comprises a filter member 54 secured by a pin 56 to mass 58. That portion of mass 58 adjacent to filter member 54 has groove 62 to receive O-ring seal 64 which forms a seal between mass 58 and the inner walls 42 of tube 32 when seal 64 nests in the groove 62. The seal 64 serves to separate filter 54 apart from chamber 50 and is of a resilient, deformable, elastomeric material. A preferred seal 64 is fabricated from natural rubber. Seal ring 64 is frictionally mounted on the mass 58 and when device 52 descends under centrifugal force, friction between seal 64 and inner walls 42 causes the seal 64 to slide upward out of groove 62 and into the smaller diameter groove 63 above it. The annular space defined by seal ring 64 has an inside diameter smaller than the diameter of groove 62 but greater than the diameter of groove 63 so that seal ring 64 is stretched when nested in groove 62 and recovers its normal size when moved to groove 63. Thus, when ring 64 is moved to groove 63, communication is established between filter member 54 and chamber 50 by ring 64 contracting to normal diameter. Device 52, comprising filter member, mass and seal ring has the specific gravity of between about 1.03 and 1.09, preferably about 1.03 to about 1.05.

Assembly 30 is operated as follows. Whole blood or anti-coagulant treated whole blood is collected in chamber 50 through a cannula inserted through penetration zone 48 of closure 40. To assist filling chamber 50, the assembly 30 may be first air evacuated in any conventional manner. Whole blood received in chamber 50 is then allowed to coagulate. This generally occurs in about 30 minutes when the assembly is allowed to stand at room temperature. Anti-coagulant treated blood of course does not require any waiting time. When plasma is desired, chamber 50 may alternatively contain a proportion of anti-coagulant such as potassium oxalate for mixing with the whole blood as it is collected within chamber 50. The whole assembly 30 is then centrifuged, to effect separation of the blood into its serum or plasma portion and its substantially cellular portion. During centrifugation, device 52 descends into the interface between serum or plasma and the substantially cellular or solid portion of the blood as previously described in relation to device 10 of FIGS. 2 and 3. Prior to centrifugation, and during filling of chamber 50 with blood, seal 64 prevents the blood from contacting the periphery 66 of filter member 54. This prevents a premature clogging of the pores in filter 54 with solid particulate matter normally found in blood. During centrifugation, the centrifugal force on mass 58 and filter member 54 causes mass 58 to move downwards carrying seal 64 which rolls upward relative to piston 58. Seal 64 then moves into groove 63 and contracts in size so that there is no contact between seal 64 and the inner wall 42 of tube 32 (shown best in FIG. 7.). This permits the displaced serum or plasma to move through the filter member 54 to the space being made available above descending device 52. During passage through filter 54 the blood serum or plasma is filtered as previously described. When descent of device 52 halts, continued displacement of serum or plasma is terminated. The separated and filtered serum or plasma may be withdrawn by removing closure 38 and decanting or by inserting a cannula through closure 38 and withdrawing the fluid by means of a syringe.

FIG. 5 is a fragmentary cross-sectional side elevation of an alternate assembly embodiment of the invention, and differs from the embodiment illustrated in FIG. 4 in respect to the form of closure 38 and device 52. The separator device of the invention is referred to by the numeral 9 in FIG. 5 and has the construction of device 9 as seen in FIG. 1 supra. Closure 74 has an annular recess 76 in the lower surface, of such dimension as to receive container 70, and close the end 78 thereby. Within recess 76 and integral with the inner wall 80 of closure 74 is a sealing ring 82 which provides a constricted area for recess 76 of smaller diameter than the diameter of tube 70. Mounted within closure 74 is the device 9, in such a manner that the filter member 12 is above the constriction formed by ring 82 and thereby sealed apart from the confines of chamber 86 as defined by tube 70. The barrier separating filter 12 from chamber 86 is formed by the mating of seal ring 82 with the body of mass 14 as shown in the FIG. 5. In the embodiment of FIG. 5, the filter member 12 is protected from premature contact with the blood mixture during filling of chamber 86. During centrifugation the centrifugal force on mass 14 causes it to slide out of engagement with seal ring 82 by moving axially downwards. During this sliding of mass 14 filter member 12 is pressed against seal 82, deforms and passes over the seal 82. Once past the seal 82, filter 12 conforms to the dimensions of tube 70 to form a sliding fit with the inner wall 90 of tube 70. In all other respects, the embodiment of FIG. 5 functions in the same manner as described for the unitary assembly of FIG. 4. The advantage of the embodiment illustrated in FIG. 5 resides in the elimination of the separate seal member 64 as described and shown in relation to FIGS. 4 and 7.

Although the above described embodiments represent preferred forms of the invention, they are not to be considered as defining the limits of the invention. For example, means of isolating the serum or plasma from the cellular elements after centrifugation may be employed. Illustrative of such means is that shown in FIG. 6, a cross-sectional, fragmentary side elevation of a unitary assembly similar to that shown in FIG. 4 except that a thin sheet 100 of blood impermeable, flexible material such as ethylene-vinyl-acetate copolymers, low density elastomeric material or like polymeric flexible material is interposed between filter 54 and mass 58. The specific gravity of sheet 100 is about 0.1 to 1.0, preferably as low as possible. Sheet 100 may be attached to bolt 56 and divides the space between mass 58 and filter 54 into an upper zone 102 and a lower zone 104. Alternatively, sheet 100 may be affixed to the upper surface 106 of mass 58 thus obviating area 104.

Sheet 100 is of such dimension as to just touch the inner walls 42 of container 32, and prevents mass transfer from cellular material into plasma or serum or vice versa. During centrifugation of the assembly to separate the blood mixture as previously detailed, the piston component 52 descends. The pressure of displaced blood serum or plasma coupled with the upwards centrifugal force on sheet 100 due to its low density forces sheet 100 to flex away from walls 42 and into area 102, providing a passageway for the displaced serum or plasma to reach filter member 54. After centrifugation sheet 100 establishes contact with walls 42 to seal area 102 from 104 and thus isolate serum or plasma from cellular material.

What is claimed:

1. An assembly for the collection, separation and filtration of the liquid portion of blood, which comprises:
   a tubular container having one open end and one closed end;
   a removable closure for said open end;
   a piston component which comprises,
   a. a cylindrical flexible filter member slidably mounted in said container so as to form a sliding fit with the inner wall of said container and having a central portion and a peripheral portion; and
   b. a mass member having a width which is less than the diameter of said filter member, said mass member being attached to the central portion of one end of said filter member so that the periphery portion of said filter member extends radially beyond said mass member, whereby said mass does not mate with the inner walls of said container, said filter member and said mass member together having a specific gravity within the range of from about 1.03 to about 1.09.

2. The assembly of claim 1 wherein said filter member is an open cell polyurethane foam.

3. The assembly of claim 1 wherein said filter member and said mass member together have a specific gravity within the range of from about 1.03 to about 1.05.

4. The assembly of claim 1 wherein said mass has a length which exceeds the diameter of said filter member.

5. The assembly of claim 1 wherein the end of said mass proximal to said filter member is conical.

6. The assembly of claim 1 wherein said mass includes a sealing O-ring circumscribing said mass at a point adjacent to said filter member.

7. An assembly for the collection, separation and filtration of the liquid portion of blood which comprises:
   a tubular container having open ends;
   a first closure sealing one of the open ends of the container and a second closure which is penetrable by a cannula sealing the other of said open ends, both of said closures being formed of self-sealing elastomeric material;
   a piston component which comprises,
   a. a flexible cylindrical filter member slidably mounted in said container so as to form a continuous sliding fit with the inner wall of said container; and
   b. a solid mass attached to the central portion of one end of said filter member said mass having a width which is less than the diameter of said filter member whereby said mass does not mate with the inner walls of said container;
   said filter member and said mass together having a specific gravity within the range of from about 1.03 to about 1.09; and
   means for preventing contact between said filter member and blood collected within said tubular container, said means being removable by a centrifugal force.

8. An assembly according to claim 7 wherein said filter member is an open cell polyurethane foam.

9. An assembly according to claim 7 wherein the specific gravity of said filter member together with said mass and said means for preventing contact is from about 1.03 to about 1.05.

10. An assembly according to claim 7 wherein said cylinder has a length which exceeds the diameter of said filter member.

11. An assembly according to claim 7 wherein said mass has a conical end and said conical end is the point of attachment to said filter member.

12. An assembly according to claim 7 wherein said means comprises a sealing ring mounted on said cylindrical mass and which in association with said cylindrical mass and the inner walls of said container seals the space between said mass and said walls below said filter member.

13. An assembly according to claim 7 wherein said means comprises a sealing ring mounted on said first closure and which in association with said mass seals the space between said mass and the inner walls of said tubular container beneath said filter member.

14. The assembly of claim 7 wherein said first closure comprises:
 a. an elastomeric plug having an annular recess in one surface thereof;
 b. an annular sealing ring integral with the interior sidewall of said recess, said ring dividing said recess into an inner and an outer zone, said outer zone being adapted to receive the open end of a tubular container;
said filter member being mounted within the inner zone of said recess and said recess and said inner zone being sealed by said means for preventing contact between said filter member and blood collected within said tubular container, said means being the mating of said cylindrical mass with said sealing ring.

* * * * *